United States Patent [19]

Pedersen

[11] Patent Number: 4,651,671
[45] Date of Patent: Mar. 24, 1987

[54] CONTINUOUS FEED APPARATUS FOR STAINING SPECIMENS CARRIED ON SLIDES

[76] Inventor: Anders N. Pedersen, 1419 Dominis St., #1503, Honolulu, Hi. 96822

[21] Appl. No.: 831,620

[22] Filed: Feb. 21, 1986

[51] Int. Cl.⁴ .......................... B05C 3/05; B05C 13/02
[52] U.S. Cl. ........................................ 118/57; 118/425
[58] Field of Search ................... 118/425, 57; 134/71, 134/73, 83, 157, 165

[56] References Cited

U.S. PATENT DOCUMENTS 3,356,096 12/1967 Davis et al. ............... 118/425 X
3,507,292 4/1970 Pedersen .................. 118/423 X Primary Examiner—Evan K. Lawrence
Attorney, Agent, or Firm—George W. T. Loo

[57] ABSTRACT

A device for transporting specimens carried on microscope slides through a plurality of liquid containing jars for staining or otherwise treating the specimens. It includes a rail, a conveyor chain, a conveyor motor, an elliptically shaped rod, a rod motor, a plurality of open top jars, a plurality of carriers, and a plurality of slide holders. The jars are positioned along a horizontal path. Each slide holder is pivotally connected to a carrier so that its slide holding portion will extend into a jar or be lifted above the jar when the rod is rotated counterclockwise 90° from its horizontal position to its vertical position. Subsequent continuous counterclockwise rotation of the rod will alternately permit slides to be lowered by gravity and raised by the force provided by the rod. The carriers and slide holders with slides attached are supported by the rail, moved horizontally by the conveyor chain parallel to the path, and agitated up and down by the rod. The rod has the double purpose of lifting slides over any obstructing jar wall and of agitating slides for faster and more uniform infiltration of the specimens.

9 Claims, 6 Drawing Figures

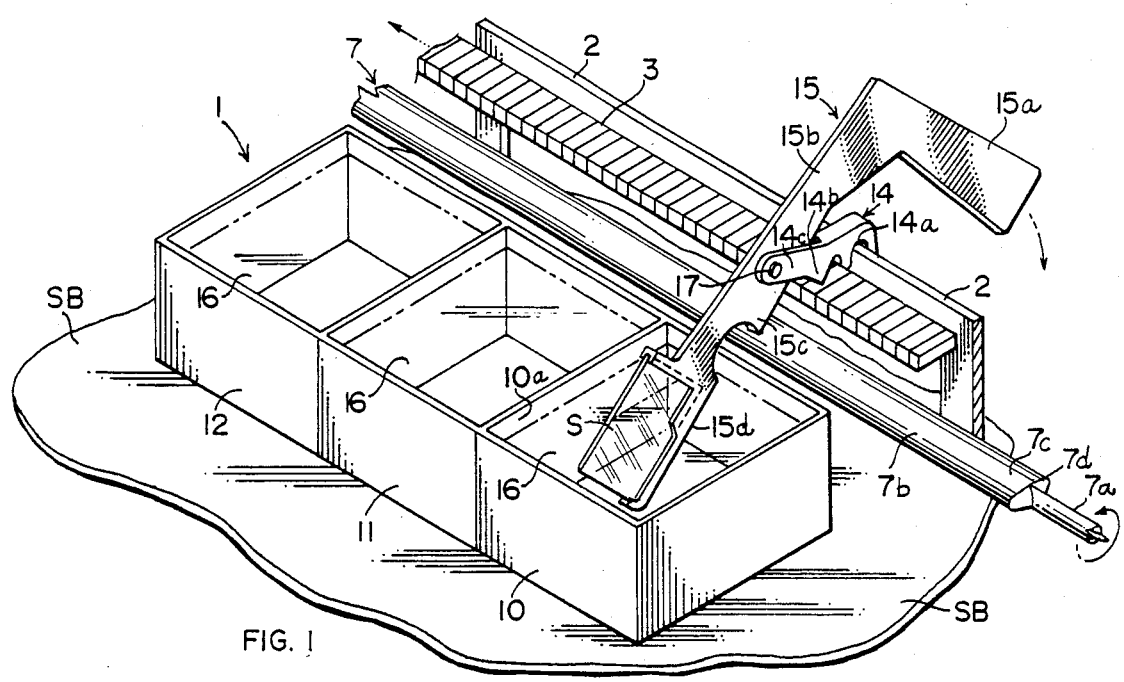
FIG. 1
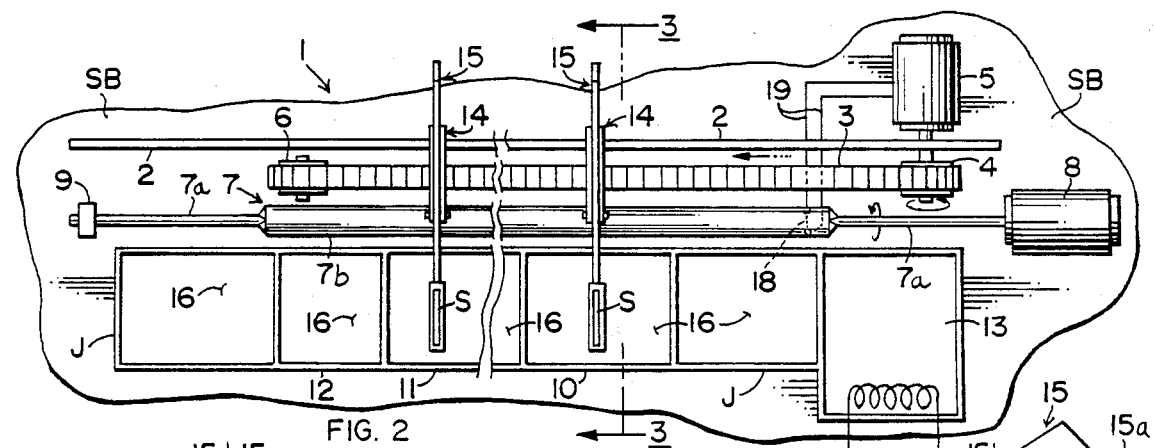
FIG. 2
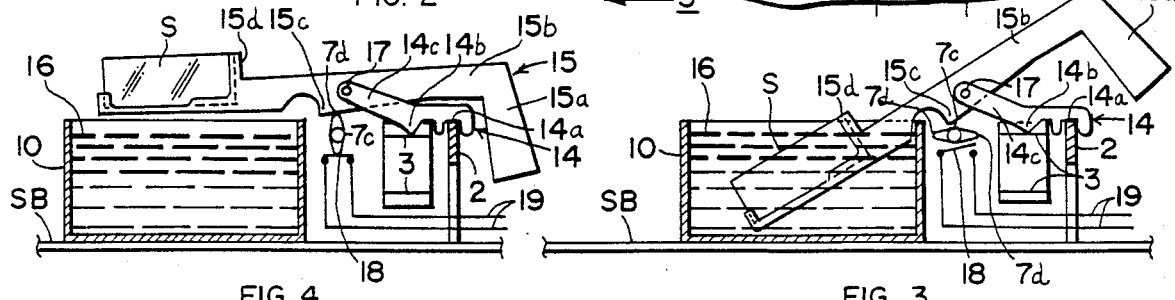
FIG 4
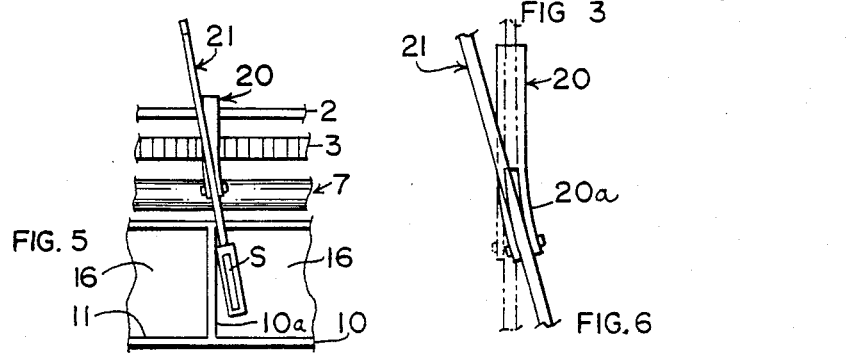
FIG. 5
FIG. 6

4,651,671

CONTINUOUS FEED APPARATUS FOR STAINING SPECIMENS CARRIED ON SLIDES

BACKGROUND OF THE INVENTION

1. Field of Invention

This invention relates to apparatus for staining specimens carried on microscope slides such as used in the pathological inspection of human tissues.

2. Description of the Prior Art

My prior invention disclosed in U.S. Pat. No. 3,507,292, issued on Apr. 21, 1970, has acquired world wide usage in the staining of thin histology sections cut from paraffin blocks. It is, however, not very well suited for procedures where time is of essence as, for example, when frozen sections are stained in less than one minute while a patient is under anesthesia. In addition it has found limited usage for thick specimens such as thick PAP-smears often encountered in cytology laboratories. My present invention is well suited for frozen section diagnosis and for the staining of thick specimens.

3. Disclosure Statement

Pedersen, U.S. Pat. No. 3,507,292, issued on Apr. 21, 1970, discloses an apparatus for staining specimens carried on microscope slides. Slide engaging bail 52 is pivotally secured to the body of carrier 34 so that a slide S which is supported on the bail can be lifted above the jar walls of jars 26, 28, 30 and 32 in passing from one jar to a succeeding jar. Bail 52 is pivoted about axis of central bight 54 in response to forward movement of the slides by provision of an oblique cam surface 74 positioned adjacent to the top of each jar at the downstream end of the jar and in the path of travel of depending portion 60 of bail 52 to lift the slide to a level sufficient to clear the upper edge of the jar wall. When the slide clears the front end of the succeeding jar it drops into the liquid medium contained in such jar and the staining process continues. Such drop is not abrupt because of the effect of counterweight 66. In order to avoid harmful drying of specimens in transit from one jar to the next, some procedures require machines that are so long that it often is a problem to fit them into existing laboratories. It does not provide uniform infiltration of specimens or the quick staining of frozen sections because of the slow horizontal movement of slides and the rather slow, friction dependent translation of a horizontal force to the vertical one, that is involved in slide lift.

My present invention utilizes a rotating rod to provide both agitation of specimen and the force necessary to raise it above any obstructing jar wall. It agitates slides for faster and more uniform infiltration of specimens. It can go deeper into a jar so that the upper part of a slide is stained and it can go faster than my prior invention. It can be used for the quick staining of frozen sections when time is of essence, for example, when a patient is under general anesthesia. The shorter time a patient is under general anesthesia the less risk for patient and, furthermore, it is expensive to keep a fully staffed operating room waiting undue long time for a frozen section diagnosis. It can be used for thick specimens such as thick PAP-smears.

SUMMARY OF THE INVENTION

This invention relates to a slide transporting apparatus that sequentially conveys specimen bearing slides into and out of a plurality of staining solutions and like media. An endless conveyor chain has in parallel spaced relation an elongated rail on one side and an elongated rod on the other side. Parallel to the rod and adjacent to it are a row of liquid media containing jars. A number of carriers and slide holders with slides attached are supported by the rail, moved horizontally by the chain, and agitated up and down by the rod. The slides are agitated for faster and better infiltration of specimens and are lifted above an obstructing jar wall by the rotation of the rod.

An object of this invention is to provide a simple and inexpensive slide staining apparatus where the mechanical means that agitate a slide also provide the force that lifts a slide above an obstructing jar wall.

Another object of this invention is to provide a continuous feed slide stainer where agitation of slides causes the infiltration to be so fast that the staining procedure is substantially expedited.

A further object of this invention is to provide a slide staining apparatus which will uniformly stain thick specimens by applying the necessary agitation.

Still another object of this invention is to provide a slide staining apparatus which will move a slide above an obstructing jar wall so fast that the specimen will not be exposed to harmful drying even when horizontal conveyor speed is very slow.

A still further object of this invention is to provide a slide staining apparatus that is very compact and easy to fit into existing laboratories.

Another object of this invention is to provide a slide staining apparatus which is well suited for procedures where time is of essence.

Other objects, features and advantages of the present invention will be readily apparent from the following detailed description taken in connection with the accompanying drawing.

BRIEF DESCRIPTION OF THE DRAWING

FIG. 1 is a schematic perspective of a slide staining apparatus constructed according to the present invention.

FIG. 2 is a plan view of the apparatus of FIG. 1.

FIG. 3 is an enlarged sectional view taken on line 3—3 of FIG. 2 showing a slide immersed in a staining solution.

FIG. 4 is an enlarged sectional view of FIG. 3, after the rod has turned 90° counterclockwise, showing a slide raised above a staining solution.

FIG. 5 is a plan view of a flexible carrier and slide holder of this invention pressed against the wall of a jar before being lifted.

FIG. 6 is an enlarged fragmentary plan view of the carrier and slide holder of FIG. 5 showing the bending of the carrier.

DESCRIPTION OF THE PREFERRED EMBODIMENT

Before explaining the present invention in detail it is to be understood that the invention is not limited in its application to the details of construction and arrangement of parts illustrated in the accompanying drawing, since the invention is capable of other embodiments and of being practiced or carried out in various ways. Also, it is to be understood that the phraseology or terminology employed herein is for the purpose of description and not of limitation.

Referring now to the drawing wherein like reference letters and numerals refer to like and corresponding parts throughout the several views, the preferred embodiment of of the invention disclosed in FIGS. 1-4 inclusive is a slide staining apparatus 1.

Slide staining apparatus 1 includes a rail 2, a conveyor chain 3, a drive sprocket 4, a conveyor drive motor 5, an idler sprocket 6, a rod 7, a rod motor 8, a bearing support 9, a plurality of open top jars 10, 11, and 12, carriers 14, and slide holders 15.

Rail 2 extends upwardly from support base SB with its upper reach in substantial parallelism to support base SB. Conveyor chain 3 is mounted in parallel spaced relation to rail 2. Conveyor chain 3 is supported adjacent to the inlet end of the staining path by drive sprocket 4, which is driven by conveyor drive motor 5, and at the outlet end by idler sprocket 6.

Rod 7 includes two rod shafts 7a and an ellipsoidal section 7b. Ellipsoidal section 7b includes two flattened portions 7c and two pointed portions 7d. Rod 7 is supported at one end by rod motor 8 and at the other end by bearing support 9. Rod 7 is mounted in parallel spaced relation to the upper reach of conveyor chain 3. Rod 7 rotates about an axis that is generally parallel to the path of conveyor chain 3 and jars.

A plurality of open top jars 10, 11, and 12 are placed on support base SB along a path parallel to the upper reach of conveyor chain 3 and rod 7. The length of the jars along the direction of the path of slide travel is selected so that the immersion time of the slides in a particular medium is established at a desired duration. If deemed desirable, the row of jars may be supplemented by special treatment sections such as a drying oven 13 or by additional jars J. See FIG. 2.

Carrier 14 includes a rail groove 14a, a downward projection 14b, and two forward arms 14c. Grove 14a fits over the top part of rail 2 and projection 14b extends into the space between two links of conveyor chain 3. Arms 14c reach above rod 7 to form a pivot connection at 17 with slide holder 15.

Slide holder 15 includes a handle 15a a body 15b, a projection 15c, and a slide holding portion 15d. Slide holding portion 15d holds a slide S. Handle 15a may be used to remove slide S from the jar and conveyor chain. Slide holder 15 is pivotally secured to carrier 14 at 17. Slide holder 15 is balanced to keep slide S immersed by gravity alone when rod 7 is in a horizontal position. See FIG. 3.

The operation of the present invention can be understood from a careful reading of FIGS. 3 and 4. They show the way a slide S is agitated for faster and better infiltration of specimen and the way it is lifted above an obstructing jar wall. FIG. 3 shows a slide S immersed in a staining solution 16 by gravity alone and rod 7 in a horizontal position. FIG. 4 shows slide S in a raised position and rod 7 in a vertical position. The raised position of slide S is caused by the 90° counterclockwise rotation of rod 7 from the position shown in FIG. 3. Pointed portion 7d rubs against projection 15c when rod 7 rotates counterclockwise from horizontal position to vertical position to impart a clockwise torque to slide holder 15 around pivot at 17. This causes slide S to rise above staining solution 16 and above an obstructing jar wall. Subsequent continuous counterclockwise rotation of rod 7 at a suitable speed will alternately permit slide S to be lowered by gravity and raised by force provided by rod 7. Inside a jar, where no jar wall is obstructing, repeated raises and dips will agitate a slide for better infiltration. When a jar wall is encountered, the same motion will enable the slide to climb over the obstruction.

Motors 5 and 8 may be synchronized by letting the electric power to motor 5 be controlled by a switch 18, that is activated by rod 7 as seen in FIGS. 3 and 4, and switch wires 19. Thus synchronized, conveyor chain 3 will only advance when slide S is in fully raised position and slide holder 15 will therefore never press against the side of a jar wall.

In the simplest version of the preferred embodiment, motors 5 and 8 are not synchronized. This means that occasionally slide holder 15 will press against the downstream wall of a jar before being lifted above the obstructing jar wall by rod 7. In order to avoid damage by possible breakage to the apparatus, carrier 14 may be made of a flexible material and permitted to bend as shown in FIGS. 5 and 6. Since for most purposes the rotational speed of rod 7 will be high relative to the speed of conveyor chain 3, it is not necessary to make carrier very flexible. In addition, the necessary flexibility may be designed into conveyor chain 3, slide holder 15 or hinge connection at 17.

In FIGS. 5 and 6, reference numeral 20 designate the flexible carrier; reference numeral 20a designate carrier arms; reference numeral 21 designate slide holder; and reference numeral 10a designate jar wall.

Flexible carrier 20 permits slide holder 21 and slide S to tilt when an obstructing jar wall 10a is encountered while the slide is in immersed position. See FIG. 5. When rod 7 rotates slide holder 21 and thereby lifts slide S, slide holder 21 will jump back to its normal position, perpendicular to rail 2, and quickly immerse in the next solution.

Arrows in FIG. 1 show the direction of movement of conveyor chain 3, rod 7, and slider holder 15. Arrows in FIG. 2 show the direction of movement of conveyor chain 3, drive sprocket 4, and rod 7. Broken lines in FIG. 6 show the normal position of carrier 20 and slide holder 21.

My invention agitates slides for faster and more uniform infiltration of specimens. It can go deeper into a jar so that the upper part of a slide is stained and it can go faster than existing slide transporting apparatus. It can be used for the quick staining of frozen section when time is of essence. It can be used for thick specimens such as thick PAP-smears. It can be made shorter so that it will easily fit into existing laboratories. It is more versatile and can be used for greater variety of procedures. My invention is a significant improvement over existing slide staining apparatus.

Although but a single embodiment of the invention has been disclosed and described herein, it is obvious that many changes may be made in the size, shape, arrangements, color and detail of the various elements of the invention without departing from the scope of the novel concepts of the present invention.

I claim as my invention:

1. Apparatus for sequentially immersing a slide mounted specimen in a plurality of liquid media comprising:
   (a) a plurality of open top jars positioned along a generally horizontal path,
   (b) conveyor means for supporting and moving objects parallel to said path,
   (c) means to agitate slides and to lift slides above jar walls,
   (d) a carrier operatively connected to the conveyor means, and (e) a slide holder pivotally connected to the carrier and including a member for mounting a slide which interacts with the slide agitating and lifting means so that the member alternately extends into the jar and is lifted above the jar.

2. The apparatus of claim 1, wherein the slide agitating and lifting means includes an elliptically shaped rod that is rotated about an axis that is generally parallel to the path of the jars by a rod motor and the major surface of the rod contacts the slide holder.

3. The apparatus of claim 2, wherein the conveyor means include a rail, a conveyor chain, and a conveyor motor; the inner side of the conveyor chain is in parallel spaced relation to the rod and the outer side of the conveyor chain is in parallel spaced relation to the rail; and the conveyor chain is operatively connected to the conveyor motor.

4. The apparatus of claim 3, wherein the conveyor motor and the rod motor are not synchronized and the carrier is made of a flexible material.

5. The apparatus of claim 3, wherein the conveyor motor and the rod motor are synchronized so that the conveyor chain will advance only when the slide holder is in its raised position.

6. A slide staining apparatus comprising a rail, a conveyor chain, a conveyor motor, a carrier, a slide holder, a plurality of open top jars, and means to agitate and lift slides above the jar walls; wherein the conveyor chain is operatively connected to the conveyor motor; the jars are positioned along a generally horizontal path; the carrier is operatively connected to the rail and conveyor chain for movement parallel to said path; the slide holder is pivotally connected to the carrier so that its slide holding portion extends into the jar and is engageable by said slide agitating and lifting means so that said portion is lifted above the jar when it is engaged by said agitating and lifting means.

7. The apparatus of claim 6, wherein the slide agitating and lifting means includes a rod that is rotated about an axis that is generally parallel to the path of the jars by a rod motor; the rod has an elliptically shaped middle section and two cylindrically shaped outer sections and the major surface of the rod contacts the slide holder.

8. The apparatus of claim 7, wherein the conveyor motor and the rod motor are not synchronized.

9. The apparatus of claim 7, wherein the conveyor motor and the rod motor are synchronized so that conveyor chain will advance only when the slide holder is in its raised position.

* * * * *